US006509312B1

(12) United States Patent
Giersch

(10) Patent No.: US 6,509,312 B1
(45) Date of Patent: Jan. 21, 2003

(54) ALIPHATIC ESTERS AND THEIR UTILIZATION AS PERFUMING INGREDIENTS

(75) Inventor: Wolfgang Klaus Giersch, Bernex (CH)

(73) Assignee: Firmenich SA, Geneva (CH)

( * ) Notice: Subject to any disclaimer, the term of this patent is extended or adjusted under 35 U.S.C. 154(b) by 199 days.

(21) Appl. No.: 09/603,685

(22) Filed: Jun. 26, 2000

(30) Foreign Application Priority Data

Jul. 14, 1999 (CH) .............................................. 1303/99

(51) Int. Cl.[7] .................................................. A61K 7/46
(52) U.S. Cl. ............................. 512/25; 512/26; 512/27; 560/1; 560/129
(58) Field of Search ............................. 512/25, 26, 27; 560/1, 129

(56) References Cited

U.S. PATENT DOCUMENTS

| | | | | |
|---|---|---|---|---|
| 5,461,099 A | | 10/1995 | Ishikawa et al. | 524/317 |
| 5,952,292 A | * | 9/1999 | Snowden et al. | 424/401 |
| 6,159,929 A | * | 12/2000 | Snowden et al. | 424/401 |

FOREIGN PATENT DOCUMENTS

| | | |
|---|---|---|
| EP | 0 659 856 | 4/1986 |
| EP | 0 178 532 B1 | 6/1990 |

OTHER PUBLICATIONS

Cainelli et al., Diastereofacial Selectivity in the Reaction of Chira N–Trimethylsilyl Imines with Ester Enolates: Preparation of trans–Azetidin–2–ones in High Stereocontrolled Fashion, Elsevier Science Ltd., *Tetrahedron* vol. 52, No. 5, pp 1685–1698 (1996).

M. Rafecas, Analysis of Volatile Compounds from a Parmesan Type Cheese by Adsorption With Activated Charcoal, *Rev. Agroquim., Technol. Aliment.* (1986) 26 (4) 597–601 (Abstract).

Patent Abstracts of Japan, vol. 18, No. 17 (E–1488), Jan. 12, 1994, JP 05 258611, Oct. 8, 1993.

* cited by examiner

*Primary Examiner*—Jill Warden
*Assistant Examiner*—Monique T. Cole
(74) *Attorney, Agent, or Firm*—Winston & Strawn

(57) ABSTRACT

The compounds of formula (I)

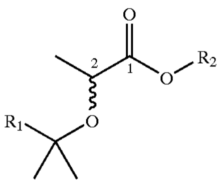

wherein $R_1$ represents a methyl or ethyl group, $R_2$ represents an ethyl group, a linear or branched propyl group, or an isobutyl group and the wavy bond indicates that the carbon number 2 is asymmetric and can adopt a configuration R or S, are useful as perfuming ingredients for the preparation of perfumes, perfuming compositions and perfumed articles. They can be used to impart a very natural fruity note.

5 Claims, No Drawings

ALIPHATIC ESTERS AND THEIR UTILIZATION AS PERFUMING INGREDIENTS

BRIEF SUMMARY OF THE INVENTION

The invention relates to the field of perfumery. It concerns a method to confer, improve, enhance or modify the odor properties of a perfuming composition or a perfumed article, which method comprises adding to said composition or article a fragrance effective amount of a compound of formula (I)

(I)

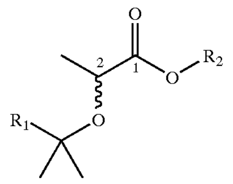

wherein $R_1$ represents a methyl or ethyl group, $R_2$ represents an ethyl group, a linear or branched propyl group, or an isobutyl group and the wavy bond indicates that the carbon number 2 is asymmetric and can adopt a configuration R or S, in the form of an optically active isomer or as a mixture of isomers, as perfuming ingredient for the preparation of perfuming compositions or perfumed articles.

The invention also concerns the compounds of formula (I) as defined above, ethyl (S)-2-tertbutoxypapanoate being excluded.

The esters of formula (I) possess very useful and prized odor properties. As a result, they can be used to prepare perfumes and perfuming compositions, as well as perfumed products to which they impart very natural fruity notes.

PRIOR ART

The compound of formula (I) wherein $R_1$ is a methyl group and $R_2$ is an ethyl group, namely ethyl (S)-2-tertbutoxypropionate, is known from the prior art. This compound is described as a synthetic intermediate by G.Cainelli, M. Panunzio, E. Bandini, G. Martelli and G. Spunta in Tetrahedron; EN; 52; 5; 1996; 1685–1698. However the prior art never mentioned a description of the odor nor of the potential use of such a compound in perfumery.

All the other compounds of formula (I) are novel.

A large number of esters of similar structure to that of compounds (I) is known from the prior art. We can quote Rev. Agroquim. Tecnol. Aliment. (1986), 26(4), 597–601 that describes the utilization of ethyl 2-ethoxypropionate as a racemic mixture for the flavoring of cheese, particularly Parmesan cheese. Many other compounds with a similar structure to that of this invention have been described in the synthetic field, however, to our knowledge, in the prior art there is no mention or suggestion of a potential use of these esters as perfuming ingredients.

DETAILED DESCRIPTION OF THE INVENTION

We have now surprisingly discovered that the compounds of formula (I) possess very unexpected olfactory properties in view of the prior art, which make their use in perfumery very attractive.

The compounds of formula (I) are characterized by an odor with a very natural fruity top note, which renders them particularly prized by the perfumers. The intensity of this note varies from a compound to another. Moreover, the associated under notes, which also change from compound to compound, make it possible to impart to a basic composition a full range of olfactory shades and thus rendering each compound able to contribute to the diversity of the perfumer's palette.

As an example, we can find in the fragrant note of several esters of the invention a connotation of the chamomile type. This note is particularly distinct in the odor of the ethyl (R)-2-(1,1-dimethylpropoxy)propionate whose fruity note is also very strong. The ethyl (S)-2-(1,1-dimethylpropoxy) propionate has a more spicy note which also comprises a chamomile type under note and other notes reminiscent of ethyl 2-acetyl-4-methyl-4-pentanoate (EP B1 0178532; origin: Firmenich S A, Geneva, Switzerland), the wine lees, linalool and also coriander. The chamomile note of the propyl (S)-2-tert-butoxypropionate is associated with a liquorice undernote having a very nice peach-apricot connotation.

The odor of isobutyl (S)-2-tert-butoxypropionate and isopropyl (S)-2-(1,1-dimethylpropoxy)propionate also has a connotation recalling the odor of chamomile, but less powerful than that of the previous compounds.

The ethyl (S)-2-tert-butoxypropionate has an odor with a fruity character, which is also velvety, ethereal, liquor-like, with further minty notes. Its fresh fragrance has the natural character common to all the compounds of the invention.

Amongst the compounds of the invention, the propyl (S)-2-(1,1-dimethylpropoxy)propionate is a choice perfuming ingredient. It has an odor with a fruity top note associated with refreshing smoky notes. The odor keeps its natural aspect. In fact it recalls the odor of the 8-p-menthen-2-ol acetate, with also a floral, linalool, citrata mint connotation. This fruity, floral note with a clary sage, citrata mint connotation has a very natural fresh character which makes it very appreciated by the perfumers. Moreover, the propyl (S)-2-(1,1-dimethylpropoxy)propionate has been compared to dihydromyrcenol (origin: International Flavor & Fragrances), known to impart fragrant notes conferring an aromatizing fresh floral effect to perfuming compositions. We have discovered, after this comparison, that the compound of the present invention shows, in a very advantageous way, an odor whose freshness is more aromatic, sage and bergamot-like, while dihydromyrcenol has a more aromatic, lavender odor. The present invention brings a new and unexpected contribution to the permanent problem of finding new perfuming ingredients susceptible of industrial preparation, of a wide use and at least as advantageous as those compounds already available on the market.

The compounds of the invention can be used in fine perfumery, in perfumes, colognes or after-shaving lotions, as well as in other current uses in perfumery such as to perfume soaps, shower or bath gels, hygiene products, hair-care products such as shampoos or conditioners or other body or air deodorants, or cosmetic preparations.

The esters (I) can also be used in applications such as liquid or solid detergents for fabric treatment, fabric softeners, detergent compositions or household products, for a domestic or industrial usc.

In these applications, the compounds of the invention can be used alone or mixed with other perfuming ingredients, solvents or usual additives in perfumery. The nature and diversity of these co-ingredients does not need to be described in a more detailed manner here, which will anyway not be exhaustive; a man skilled in the art will be able to choose such ingredients, helped by his general knowledge, according to the type of the product to be perfumed and the desired olfactory effect.

These perfuming ingredients belong to various chemical classes such as alcohols, aldehydes, ketones, esters, ethers, acetates, nitrites, terpenic hydrocarbons, heterocyclic compounds containing sulfur or nitrogen, and essential oils of synthetic or natural origin. Besides, many of these ingredients are listed in reference texts such as the book of S. Arctander, Perfume and Flavor Chemicals, 1969, Montclair, N.J. USA, or its more recent versions, or in books of similar content.

The proportions in which the compounds of the invention can be added to the products mentioned above vary within a large range of values. These values depend on the nature of the product to be perfumed and on the desired olfactory effect and, in a given composition where the compounds of the invention are mixed with perfuming ingredients or solvents or usual additives in perfumery, on the nature of the co-ingredients.

As an example, one can cite typical concentrations of the order of 5% to 30%, possibly more, by weight of the compound, relative to the weight of the perfuming composition to which it is added. Lower concentrations than previously mentioned can be used when these compounds are directly used to perfume the various consumer goods cited above.

The compounds of formula (I) are obtained in one or two steps from ethyl lactate in its optically active configuration or as a mixture of isomers, according to the following general scheme:

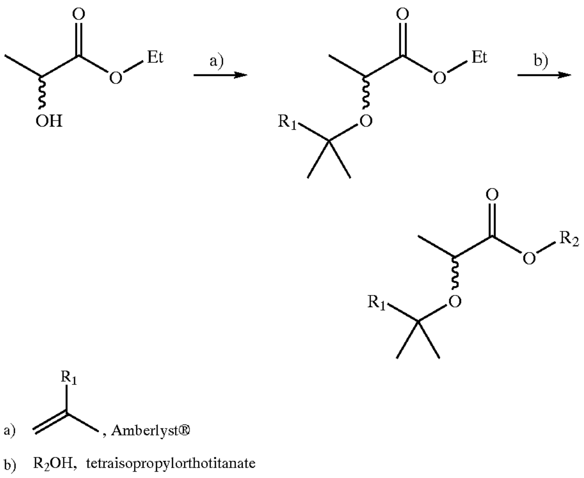

wherein the symbols have the same meaning as in formula (I). In the first step, the hydroxyl group of the ethyl lactate is alkylated; then, if required, a trans-esterification of the compound obtained previously gives the desired ester. These two steps are standard reactions, well known to a man skilled in the art.

The invention will now be described in a more detailed way using the following examples, in which the temperatures are in degrees Celsius and the abbreviations have the usual meaning in the art.

EXAMPLE 1

Preparation of the Compounds of Formula (I)

a) Ethyl (S)-2-(1,1-dimethylpropoxy)propionate

A mixture of 3534 g (50.5 mole) of isoamylene, 600 g (5.08 mole, $[\alpha]^D_{20}$=−12.4°) of ethyl (S)-lactate and 20 g of Amberlyst® 15 was kept at 10° under stirring for 66 h. The mixture obtained was filtered and then washed three times with 1 l of 10% $Na_2CO_3$ in water. After distillation (bath at 110°, pressure=20×10$^2$ Pa) 692.2 g of ethyl (S)-2-(1,1-dimethylpropxy)propionate are obtained (95% purity and 69% yield).

Analytical data: b.p. (20×10$^2$ Pa)=80°

$[\alpha]^D_{20}$=−42.21° ($CHCl_3$)

NMR($^1$H) (360 MHz; $CDCl_3$): 0.89(t, J=7.2 Hz, 3H); 1.13(s, 3H); 1.14(s, 3H); 1.27(t, J=7.2 Hz, 3H); 1.33(d, J=7.2 Hz, 3H); 4.1(q, J=7.2 Hz, 1H); 4.18(double q, J=7.2 Hz, 2H).

MS: 188(M$^+$, 0), 173(3), 159(18), 115(19), 101(21), 71(100), 43(65).

b) Propyl (S)-2-(1,1-dimethylpropoxy)propionate 535 g (2.8 mole) of ethyl (S)-2-(1,1-dimethylpropxy) propionate, obtained according to a) and 8 g (28 mmole) of tetraisopropylorthotitanate (origin: Fluka), were added to 430 g (7.1 mole) of propanol and the mixture heated at reflux, with stirring. The ethanol produced was separated by distillation using a Vigreux column (max. head temperature: 95°). After cooling, the mixture was washed successively with a 10% HCl/ice mixture, water, a $NaHCO_3$ solution and then brine. 539 g of propyl (S)-2-(1,1-dimethylpropxy) propionate were obtained (purity: 97.2%; yield: 94%).

Analytical data: b.p. (20×10$^2$ Pa)=83°

$[\alpha]^D_{20}$=−49° ($CHCl_3$)

NMR($^1$H) (360 MHz; $CDCl_3$): 0.89(t, J=7.2 Hz, 3H); 0.96(t, J=7.2 Hz, 3H); 1.13(s, 3H); 1.14(s, 3H); 1.35(d, J=7.2 Hz, 3H); 4.08(t, J=7.2 Hz, 2H); 4.11(q, J=7.2 Hz, 1H).

NMR($^{13}$C) (90.5 MHz; $CDCl_3$): 8.5(q); 10.4(q); 20.5(q); 22.0(t); 25.1(q); 33.5(t); 66.2(t); 67.3(d); 175.2(s).

MS: 202(M$^+$, 0), 187(1), 173(11), 131(9), 115(27), 71(100), 43(52).

c,d) Isobutyl (S)-2-(1,1-dimethylpropoxy)propionate and isopropyl (S)-2-(1,1-dimethylpropoxy)propionate These two compounds have been synthesized in two steps. The first one is described in a). The second one has been performed according to an experimental procedure similar to the one described in b), using the appropriate alcohol as reactant according to the desired final product (see scheme 1).

Analytical data:

Isobutyl (S)-2-(1,1-dimethylpropoxy)propionate $[\alpha]^D_{20}$=−46.1° ($CHCl_3$)

NMR($^1$H) (360 MHz; $CDCl_3$): 0.89(t, J=7 Hz, 3H); 0.95(t, J=7 Hz, 6H); 1.30 and 1.35(2s, 6H); 1.36(d, J=7 Hz, 3H); 3.9(d, J=7 Hz, 2H); 4.12(q, J=7 Hz, 1H).

NMR($^{13}$C) (90.5 MHz; $CDCl_3$): 8.5(q); 19.1(q); 20.6(q); 25.0(q); 27.8(d); 33.5(t); 67.2(d); 70.7(t); 77.1(s); 175.2(s).

MS: 216(M$^+$, 0), 187(4), 145(3), 131(20), 115(25), 71(100), 43(40).

Isopropyl (S)-2-(1,1-dimethylpropoxy)propionate $[\alpha]^D_{20}$=−49.2° ($CHCl_3$)

NMR($^1$H) (360 MHz; $CDCl_3$): 0.89(t, J=7 Hz, 3H); 1.30 et 1.35(2s, 6H); 1.50 and 1.52(2d, J=7 Hz, 6H); 1.32(d, J=7 Hz, 3H); 4.06(q, J=7 Hz, 1H); 5.04(hept., J=7 Hz, 1H).

NMR($^{13}$C) (90.5 MHz; $CDCl_3$): 8.5(q); 20.4(q); 21.7(2q); 25(q); 25.1(q); 33.5(t); 67.4(d); 67.8(d); 174.7(s).

MS: 202(M$^+$, 0), 173(6), 145(5), 131(19), 115(20), 71(100), 59(20), 43(47).

e) Ethyl (S)-2-tert-butoxypropionate

The compound has been obtained according to an experimental procedure similar to that described in a), by choosing the correct reactant as described in scheme 1 (step Analytical data:

$[\alpha]^D_{20}$=−41° ($CHCl_3$)

NMR($^1$H) (360 MHz, $CDCl_3$): 1.20(s, 9H); 1.28(t, J=8 Hz, 3H); 1.35(d, J=8 Hz, 3H);4.11(q, J=7 Hz, 1H);4.19(dq, J=1.7 Hz, 2H).

NMR($^{13}$C) (90.5 MHz, $CDCl_3$): 14.2(q); 20.5(q); 27.8(q); 60.6(t); 67.6(d); 74.8(s); 175.1(s).

MS: 174($M^+$, 1), 159(4), 101(40), 73(12), 57(100), 45(10), 41(21), 39(6), 29(19), 27(8).

f,g) Propyl (S)-2-tert-butoxypropionate and isobutyl (S)-2-tert-butoxypropionate These two compounds have been synthesized in two steps. The first one is described in e). The second one has been performed according to an experimental procedure similar to the one described in b), using the appropriate alcohol as reactant according to the desired final product (see scheme 1).

Analytical data:

Propyl (S)-2-tert-butoxypropionate $[\alpha]^D_{20}$=−50° ($CHCl_3$)

NMR($^1$H) (360 MHz, $CDCl_3$): 0.96(t, J=7 Hz, 3H); 1.20(s, 9H); 1.34(d, J=7 Hz, 3H); 1.68(m, 2H); 4.09(m, 2H); 4.12(q, J=7 Hz, 1H).

NMR($^{13}$C) (90.5 MHz, $CDCl_3$): 10.4(q); 20.6(q); 22.0(t); 27.8(q); 66.3(t); 67.6(d); 74.8(s); 175.2(s).

MS: 188($M^+$, <0.5), 173(3), 101(60), 57(100).

Isobutyl (S)-2-tert-butoxypropionate $[\alpha]^D_{20}$=−49.2° ($CHCl_3$)

NMR($^1$H) (360 MHz, $CDCl_3$): 0.94(2d, J=7 Hz, 6H); 1.20(s, 9H); 1.35(d, J=7 Hz, 3H); 3.90(d, J=7 Hz, 2H); 4.13(q, J=7 Hz, 1H).

NMR($^{13}$C) (90.5 MHz, $CDCl_3$): 19.1(2q); 20.6(q); 27.8 (d); 27.8(q); 67.5(d); 70.8(t); 74.8(s); 175.1(s).

MS: 202($M^+$, <0.5), 131(5), 101(30), 57(100).

h) Ethyl (R)-2-(1,1-dimethylpropoxy)propionate

The compound has been obtained according to an experimental procedure similar to that described in a), using the ethyl (R)-lactate ($[\alpha]^D_{20}$=+11°) as starting material.

Analytical data:

$[\alpha]^D_{20}$=+48.8° ($CHCl_3$)

NMR($^1$H) (360 MHz, $CDCl_3$): 0.89(t, J=7 Hz, 3H); 1.30 et 1.35(2s, 6H); 1.28(t, J=7 Hz, 3H); 1.34(d, J=7 Hz, 3H); 4.1(q, J=7 Hz, 1H); 4.19(double q, J=7 Hz, 2H).

MS: 188($M^+$, 0), 173(4), 159(13), 115(18), 101(16), 71(100), 55(15), 43(62).

i) Propyl (R)-2-(1,1-dimethylpropoxy)propionate

These two compounds have been synthesized in two steps. The first one is described in h). The second one has been performed according to an experimental procedure similar to the one described in b), using the appropriate alcohol as reactant according to the desired final product (see scheme 1).

Analytical data:

$[\alpha]^D_{20}$=+51° ($CHCl_3$)

NMR($^1$H) (360 MHz, $CDCl_3$): 0.89(t, J=7 Hz, 3H); 0.96(t, J=7 Hz, 3H); 1.30 and 1.35(2s, 6H); 1.35(d, J=7 Hz, 3H); 4.08(t, J=7 Hz, 2H); 4.10(q, J=7 Hz, 1H).

MS: 202($M^+$, 0), 187(3), 173(13), 131(10), 115(36), 71(100), 43(36).

EXAMPLE 2

Preparation of a Perfuming Composition for a Masculine Cologne

A base composition intended for a masculine Cologne was prepared from the following ingredients:

| Ingredients | Parts by weight |
|---|---|
| Benzyl acetate | 40 |
| Geranyl acetate | 10 |
| Linalyl acetate | 100 |
| Cedarleaf[1)] | 20 |
| Allyl amyl glycolate | 10 |
| Ambrox ®[2)] | 20 |
| Aspic essential oil | 100 |
| Bergamot essential oil | 180 |
| Citral[3)] | 30 |
| Coumarin | 20 |
| Tarragon essential oil | 10 |
| Synth Juniper essential oil | 40 |
| English clove essential oil | 10 |
| Lavandin essential oil | 120 |
| Linalol | 170 |
| Lyral ®[4)] | 60 |
| Mandarin essential oil | 30 |
| Crystal moss | 50 |
| 10% * Rose oxide | 20 |
| Siberian pine essential oil | 20 |
| Patchouli essential oil | 150 |
| Polysantol ®[5)] | 30 |
| Amyl salicylate | 20 |
| Benzyl salicylate | 440 |
| Ylang extra | 30 |
| 10% * Zestover[6)] | 70 |
| Total | 1800 |

* in dipropylene glycol
[1)]Origin: Givaudan-Roure SA, Vernier, Switzerland
[2)]8,12-epoxy-13,14,15,16-tetranorlabdane; origin: Firmenich SA, Geneva, Switzerland
[3)]Origin: Firmenich SA, Geneva, Switzerland
[4)]4-(4-hydroxy-4-methylpentyl)-3-cyclohexene-1-carbaldehyde; origin: International Flavors & Fragrances, USA
[5)]3,3-dimethyl-5-(2,2,3-trimethyl-3-cyclopenten-1-yl)-4-penten-2-ol; origin: Firmenich SA, Geneva, Switzerland
[6)]2,4-dimethyl-3-cyclohexene-1-carbaldehyde; origin: Firmenich SA, Geneva, Switzerland The addition of 300 parts by weight of propyl (S)-2-(1, 1-dimethylpropoxy)propionate to this composition allows to obtain a new composition with an odor which has a distinct fresh-herbaceous connotation, slightly citrus. The diffusion of the odor is clearly enhanced when compared with that of the base composition. Moreover, the fragrant notes of this new composition render it more voluminous and more sparkling.

EXAMPLE 3

Preparation of a Perfuming Composition for a Body Deodorant

A base composition intended for a body deodorant was prepared from the following ingredients:

| Ingredients | Parts by weight |
|---|---|
| Allyl amyl glycolate | 20 |
| 10% * Ambrox ®[1)] | 15 |
| Bergamot synth. | 180 |
| 1% * Civet synth. | 30 |
| 10% * α-Damascone | 50 |
| Lorysia ®[2)] | 10 |
| Galaxolide ®[3)] 50 MIP | 45 |
| Galbex ®[4)] | 30 |
| Chinese geranium essential oil | 15 |
| Hedione ®[5)] | 60 |
| 10% * Indolene | 10 |
| Iso E super[6)] | 10 |
| Iralia ®[7)] | 10 |
| Lavandin grosso | 50 |

-continued

| Ingredients | Parts by weight |
|---|---|
| Lyral ®[8] | 15 |
| 10% * Crystal moss | 50 |
| Tonalide ®[9] | 40 |
| Vertofix coeur[10] | 110 |
| Total | 750 |

* in dipropylene glycol
[1]8,12-epoxy-13,14,15,16-tetranorlabdane; origin: Firmenich SA, Geneva, Switzerland
[2]4-(1,1-dimethyl)-1-cyclohexyl acetate; origin: Firmenich SA, Geneva, Switzerland
[3]1,3,4,6,7,8-hexahydro-4,6,6,7,8,8-hexamethyl-cyclopenta-g-2-benzopyrane; origin: International Flavors & Fragrances, USA
[4]Origin: Firmenich SA, Geneva, Switzerland
[5]Methyl dihydrojasmonate; origin: Firmenich SA, Geneva, Switzerland
[6]1-(octahydro-2,3,8,8-tetramethyl-2-naphthalenyl)-1-ethanone; origin: International Flavors & Fragrances, USA
[7]Mixture of methylionone isomers
[8]4-(4-hydroxy-4-methylpentyl)-3-cyclohexene-1-carbaldehyde; origin: International Flavors & Fragrances
[9](5,6,7,8-tetrahydro-3,5,5,6,8,8-hexamethyl-2-naphthyl)-1-ethanone; origin: PWF, Holland
[10]Origin: International Flavors & Fragrances, USA Addition of 200 parts by weight of propyl (S)-2-(1,1-dimethylpropoxy)propionate to this base composition, which has an odor with a fresh deodorant connotation, clearly increases the freshness of the top note and the impact of the perfume and enhances the fragrant note imparted by the lavandin and adds to it a herbal connotation of the clary sage type.

What is claimed is:

1. A method to confer, improve, enhance or modify the odor properties or a perfuming composition or a perfumed article, which method comprises adding to said composition or article a fragrance effective amount of a compound of formula (I)

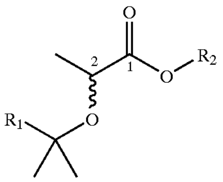

(I)

wherein the wavy bond indicates that the carbon number 2 is asymmetric and can adopt a configuration R or S, $R_1$ represents a methyl or ethyl group and $R_2$ represents an ethyl group, a linear or branched propyl group, or an isobutyl group, in the form of an optically active isomer or of a mixture of isomers.

2. A perfuming composition or perfumed article containing, together with other perfuming ingredients, solvents or adjuvants of current use in perfumery, a compound of formula (I) as defined in claim 1.

3. A perfumed article according to claim 2, in the form of a perfume, a Cologne, an after-shave lotion, a cosmetic preparation, a soap, a shampoo or hair conditioner or other hair-care product, a shower or bath gel, a body or air deodorant, a detergent or a fabric softener or a household product.

4. A compound of formula (I) such as defined in claim 1, ethyl (S)-2-tert-butoxy-propionate being excluded.

5. A compound according to claim 4, propyl (S)-2-(1,1-dimethylpropoxy)propionate.

* * * * *